United States Patent [19]
Cheng et al.

[11] Patent Number: 5,531,991
[45] Date of Patent: Jul. 2, 1996

[54] **COMPOSITION AND METHOD FOR TREATING HYPERGLYCEMIA UTILIZING AN EXTRACT OF *POLYGONUM MULTIFLORUM***

[75] Inventors: Nan-Zheng Cheng, Beltsville, Md.; Barbara Stoecker, Stillwater, Okla.

[73] Assignee: The Board of Regents of Oklahoma State University, Stillwater, Okla.

[21] Appl. No.: 237,627

[22] Filed: May 4, 1994

[51] Int. Cl.$^6$ ................................................ A61K 35/78
[52] U.S. Cl. ........................................ 424/195.1; 514/866
[58] Field of Search .......................... 424/195.1; 514/866

[56] References Cited

U.S. PATENT DOCUMENTS

| | | | |
|---|---|---|---|
| 4,797,421 | 1/1989 | Ariga et al. | 514/844 |
| 4,883,651 | 11/1989 | Meyer | 424/47 |
| 5,135,010 | 8/1992 | Fan | 131/359 |
| 5,135,746 | 8/1992 | Matsuno et al. | 424/195 |
| 5,178,865 | 1/1993 | Ho et al. | 424/195 |

OTHER PUBLICATIONS

Chem. Abstr. 102: 84480s, 1985.

"Stilbene Glycoside Gallates and Proanthocyanidins from *Polygonum multiflorum*" by Nonaka et al. rec'd Jun. 4, 1981, pp. 429 to 432 of vol. 21 *Phytochemistry*, No. 2.

"Effects of a Traditional Chinese Medicine on Lipid Metabolism of Mice" by Cheng et al, printed Mar. 20, 1988 in *The FASEB Journal* abstract 4689.

"Blood Tonics" by Daniel Reid, p. 150 of *Chinese Herbal Medicine* 1990.

Database WPI, Section Ch, Week, 8120, Derwent Publications Ltd., London, GB; class B04, AN 81–35396D & JP, A, 56 032 418 (Sunstar Hamigaki KK) 1 Apr. 1981 Abstract.

Database WPI, Section Ch, Week 9344, Derwent Publications Ltd., London, GB; Class B04, AN 93–345489 & CN, A, 1 067 179 (WU S) 23 Dec. 1992 Abstract.

*Primary Examiner*—John W. Rollins
*Attorney, Agent, or Firm*—Head Johnson & Kachigian

[57] ABSTRACT

A composition and method for treating hyperglycemia which utilize an extract of the Chinese herb *Polygonum multiflorum*. The herb is extracted with 0.1N $NH_4OH$ and centrifuged. The supernatant is applied to a Sephadex G-25 column. Three fractions are collected. The fractions exhibit a high insulin potentiating activity in fat cell assays and are shown to lower blood glucose levels.

7 Claims, No Drawings

COMPOSITION AND METHOD FOR TREATING HYPERGLYCEMIA UTILIZING AN EXTRACT OF *POLYGONUM MULTIFLORUM* has established the following criteria for classifying these illnesses.

TABLE 1

DIAGNOSTIC CRITERIA OF THE NATIONAL DIABETES DATA GROUP

| | Criteria for Diagnosis of Diabetes Mellitus and Impaired Glucose Tolerance (All plasma glucose values in mg/dL) | | | | | | Criteria for Diagnosis of Gestational Diabetes |
|---|---|---|---|---|---|---|---|
| | Normal | | Diabetes Mellitus | | Impaired Glucose Tolerance | | (100 gm OGTT) Venous Plasma |
| | Adult | Child | Adult | Child | Adult | Child | Glucose |
| FPG | <115 | <130 | ≧140 | ≧140 | 115–139 | 130–139 | Fasting ≧ 105 mg/dL |
| OGTT | <140 | <140 | ≧200 | ≧200 | 140–199 | 140–199 | 1h ≧ 190 mg/dL |
| | | | | | | | 2h ≧ 165 mg/dL |
| | | | | | | | 3h ≧ 145 mg/dL |

FPG = fasting plasma glucose;
OGTT = oral glucose tolerance test (at least 2 values).
From Harris M., et al for the National Diabetes Group: "Classification and diagnosis of diabetes mellitus and other categories of glucose intolerance." Diabetes 28:1049, 1979. Copyright 1979 by American Diabetes Association, Inc.

BACKGROUND OF THE INVENTION

This invention relates to the use of fractions of an extract of a Chinese herb in treating hyperglycemia.

The monosaccharide carbohydrate glucose is present in the blood of animals. It is the body's primary source of energy for cell metabolism, and it comes principally from the digestion of other carbohydrates. Despite wide variations in carbohydrate intake, and consequent large fluctuations in the amount of glucose absorbed by the body, the concentration of glucose in the blood, commonly referred to as the blood sugar level, is normally kept within narrow limits. In humans fasting blood glucose concentrations are considered normal if between 70 mg/dl and 114 mg/dl.

The maintenance of normal blood sugar levels is achieved by the actions of several hormones, most notably insulin, but also glucagon, epinephrine, corticosteroids, and growth hormone. Hypoglycemia, or low blood sugar, is characterized by below normal levels of blood glucose. On the other hand, hyperglycemia is exemplified by higher than normal concentrations of glucose in the blood. A substance which functions to decrease blood glucose levels is said to exhibit a hypoglycemic effect. Such a substance is sometimes called a hypoglycemic agent.

The pancreas produces insulin which is released in response to increased blood glucose concentrations. Insulin works to lower the blood sugar level by stimulating the uptake of glucose by cells. Glucose is either used in cellular metabolism to produce energy, converted to glycogen for storage in the liver and muscles, or used in the production of triglycerides and fats. As opposed to insulin, glucagon, epinephrine and corticosteroids all operate to increase blood glucose concentrations.

Many persons are afflicted with one of a genetically and clinically heterogeneous group of disorders that have glucose intolerance (hyperglycemia) in common. A good synopsis of these disorders is contained in *The Merck Manual of Diagnosis and Therapy* (Robert Berkow et al. eds., 16th ed., 1992). Impaired glucose tolerance, gestational diabetes and diabetes mellitus are diagnosed according to plasma glucose values in mg/dl. The National Diabetes Data Group The most well known of these disorders is diabetes mellitus. Diabetes mellitus is characterized by hyperglycemia resulting from impaired insulin secretion and is associated with a host of late complications including retinopathy, nephropathy, atherosclerotic coronary and peripheral arterial disease, and peripheral and autonomic neuropathies. There are two main types of diabetes mellitus. In Type I, or insulin dependent diabetes (also known as juvenile diabetes), the insulin-secreting cells in the pancreas are destroyed and insulin production ceases almost completely. Type II, or non-insulin-dependent diabetes (adult-onset diabetes), is usually marked by gradual onset wherein insulin is produced, but not in sufficient quantity to fully metabolize blood glucose. Both types result in an abnormally high level of glucose in the blood, which, if left uncorrected, can cause coma and death. In the United States alone about 150 to 200 persons per 100,000 have the insulin-dependent form of diabetes, while as many as 2,000 persons out of every 100,000 are affected with the more common Type II form.

There is good evidence that hyperglycemia conveys risks for all of the common late complications of diabetes mellitus, which are the major causes of excess morbidity and mortality in diabetics. However, there is no generally applicable and consistently effective means of maintaining normal plasma glucose fluctuations in diabetics, and efforts to do so entail significant risks of causing frequent or severe hypoglycemic episodes. Nevertheless, common treatments include diet management and the use of insulin preparations and oral hypoglycemic agents.

Insulin preparations are classified as short, intermediate or long-acting. Preparations of purified porcine insulin, purified bovine insulin, semisynthetic human insulin, and biosynthetic human insulin are now available. Conventional insulin treatment includes one or two injections per day of intermediate-acting insulin, with or without smaller added doses of rapid-acting insulin in the same syringe. Complications of insulin treatment include severe hypoglycemia, local allergic reactions, generalized insulin allergy, immunologic insulin resistance and local fat atrophy or hypertrophy.

Oral hypoglycemic agents are not used to treat insulin-dependent diabetes because they cannot prevent symptomatic hyperglycemia, but such agents can be effective when used in the treatment of non-insulin-dependent diabetes and other forms of glucose intolerance. Biguanides and sulfonylureas are the two historical classes of oral hypoglycemic agents. Biguanides, however, are not currently approved for treatment of diabetes in the United States. The sulfonylureas include tolbutamide, chlorpropamide, acetohexamide, tolazamide, glyburide and glipizide and lower plasma glucose by stimulating insulin secretion and also by enhancing insulin effect in some target tissues and inhibiting hepatic glucose synthesis. Authorities differ in the extent to which they recommend sulfonylureas. It is said that the sulfonylureas do not provide a rapid and consistently effective means of treating or preventing symptomatic hyperglycemia in patients with non-insulin-dependent diabetes, and in asymptomatic obese patients they are not consistently effective either in decreasing the hyperglycemia or in maintaining the commonly recommended target levels of plasma glucose. Hypoglycemia is the most important complication of sulfonylurea treatment. Sufonylurea-induced hypoglycemia can be severe and may last or recur for days after treatment is stopped. It is recommended that sulfonylurea-treated patients who develop hypoglycemia should be hospitalized and closely monitored, even if they respond rapidly to initial treatment for hypoglycemia, as a mortality rate of 4.3% in patients hospitalized with sulfonylurea-induced hypoglycemia has been reported.

Considering the complications attendant to the use of insulin preparations and sulfonylureas in controlling blood glucose concentrations, there is a need for a new composition and method for treating hyperglycemia that is useful in the control of the high blood glucose levels associated with glucose intolerance, but that utilizes an organically derived composition which is easy to manufacture and relatively inexpensive. Preferably the new composition would be useful in treating non-insulin-dependent hyperglycemia and would provide an alternative to the use of sulfonylureas.

SUMMARY OF THE INVENTION

It is therefore an object of this invention to overcome the limitations of the prior art by providing, as an adjunct to insulin therapy, a new composition and method for treating hyperglycemia, which composition and method do not utilize insulin preparations or common sulfonylureas, but instead use a substance that is organically derived.

It is another object of this invention to provide a composition and method for treating hyperglycemia that employ a substance having a high insulin potentiating activity.

It is a further object of this invention to provide a composition and method for treating hyperglycemia using the most potent fraction of an extract of a naturally occurring plant.

These and other objects are achieved by providing a composition and method for treating hyperglycemia which utilize an extract of a Chinese herb. The present invention uses an extract of the herb *Polygonum multiflorum* to obtain hypoglycemic effects. The herb is shown to have a high insulin potentiating activity. For use in the preferred embodiment of the present invention, the root of *P. multiflorum* is extracted with 0.1 N $NH_4OH$ (20:1) (w/v) and centrifuged (1,000×g). The supernatant is applied to a Sephadex G-25 column (50–150 u of particle size, 60×2.6 cm). Three fractions are collected and evaporated at room temperature to one-third to one-tenth of their original volume. The fractions exhibit a high insulin potentiating activity in fat cell assays and are shown to lower blood glucose level in a feeding trial. The fractions, and particularly fraction 1, exhibit a significant hypoglycemic effect.

A better understanding of the invention, and the objects thereof, will be obtained from the following detailed description.

DETAILED DESCRIPTION OF THE PREFERRED EMBODIMENT

Chinese herbs have long been used in the treatment of an almost limitless list of maladies. Around the third century B.C., the book Nei Ching, popularly known as the Yellow Emperor's Classics of Internal Medicine, was authored by a group of Chinese physicians. Among other things, this book outlined the use of herbal treatments for a variety of bodily ailments. It is said to be the fundamental text of Chinese medicine. The first Chinese classic exclusively dealing with herbal medicine, the Classic of the Agriculture Emperor's Materia Medica, was published prior to the establishment of the East Han Dynasty (A.D. 25–220) and lists a total of 365 herbs, including 252 plants, 67 animals, and 46 minerals said to be effective in treating 170 various diseases or afflictions. The classic An Outline of Matella Medica written by Shih-Chen Li and published in 1578 contains approximately 1,900,000 Chinese ideograms and a list of 1,892 herbs along with 11,096 herbal formulas. Modern day descriptions of herbs and their traditional usage can be found in Lu, Henry C., *Legendary Chinese Healing Herbs* (1991) and Reid, Daniel P., *Chinese Herbal Medicine* (1990).

In the first study conducted relating to the composition and method of the present invention, 24 Chinese herbs were assayed for their insulin potentiating activity. The Chinese herb of the present invention was selected for further study based upon the assay results.

The 24 herbs were separately stirred with a 20-fold excess (w/v) of 0.1N $NH_4OH$ for 2 hours and then centrifuged at 1,000×g for 20 minutes. Insulin potentiating activity of the supernatant of each Chinese herb extraction was evaluated using isolated adipocytes from rat epididymal fat tissue.

Plastic containers were used exclusively for fat cell isolation and assay. Two rats were sacrificed by decapitation and their epididymal fat pads removed. The distal portion of the fat pads was rinsed with 0.9% NaCl, minced with scissors, and incubated at 37° C. for 40 minutes in 6 ml of Krebs Ringer Phosphate (KRP) buffer containing 12 mg of collagenase in a water bath shaker at 200 rpm. The KRP contained 118 mM NaCl, 1.3 mM $CaCl_2$, 1.2 mM $MgSO_4$, 1 mM $KH_2PO_4$, and 16.2 mM $Na_2HPO_4$-HCl (pH 7.4). The digested tissue was passed through a silk screen using a 10-ml syringe. The preparation was then washed three times by centrifugation with KRP containing 2% albumin. Both KRP and KRP-albumin were millipore filtered and gassed with $O_2$. The material below the floating fat cells and any fat above the adipocytes were removed by aspiration. KRP-albumin (10 ml) was added to disperse the washed fat cells. Fats cells remained viable for at least 4 hours.

Insulin and the indicated amount of sample to be tested were added to tubes that contained 1.9 ml of KRP-albumin, 0.4 uCi(U-$^{14}$C) glucose (313 Ci/mol), and 67.5 ug of dextrose. Adipocytes (0.06 ml) were added, and caps containing center wells were used to seal the tubes. After incubation for 2 hours at 37° C. and shaking at 150 rpm, 0.2 ml of hyamine hydroxide was added to the center well, and 0.3 ml of 2N $H_2SO_4$ was injected into the incubation mixture to stop the reaction. The tubes were incubated for 30 minutes to allow the hyamine hydroxide to trap $^{14}CO_2$. The center wells were removed, carefully wiped, and added to 10 ml of Aquasol II and counted in a beta counter.

As shown in Table 2 below, the insulin potentiating activity of Chinese herb No. 13 (*P. multiflorum*) was higher than all other Chinese herbs tested. It was thus recognized that *P. multiflorum*, due to its high insulin potentiating activity in vitro, might enhance glucose utilization.

TABLE 2

INSULIN POTENTIATION OF CHINESE HERBS

| SAMPLES | INSULIN POTENTIATION |
|---|---|
| Standard Yeast #1 | 2.9 |
| Standard Yeast #2 | 1.7 |
| No. 1 | 0.9 |
| No. 2 | 1.1 |
| No. 3 | 0.6 |
| No. 4 | 0.5 |
| No. 5 | 1.5 |
| No. 6 | 1.1 |
| No. 7 | 1.0 |
| No. 8 | 1.1 |
| No. 9 | 1.3 |
| No. 10 | 0.8 |
| No. 11 | 1.2 |
| No. 12 | 2.1 |
| Polygonum multiflorum | 4.1 |
| No. 14 | 0.9 |
| No. 15 | 1.2 |
| No. 16 | 1.3 |
| No. 17 | 1.2 |
| No. 18 | 1.2 |
| No. 19 | 1.2 |
| No. 20 | 1.2 |
| No. 21 | 1.3 |
| No. 22 | 1.0 |
| No. 23 | 1.1 |
| No. 24 | 1.1 |

The contemporary Chinese medicinal usage of the herb *Polygonum multiflorum*, also known as He Shou Wu and more commonly as "knotgrass," is said to show effectiveness against high blood pressure and hardening of the veins and arteries. There have been several studies of *P. multiflorum* in animals, but very little is known of its physiological and chemical properties, especially as related to glucose metabolism.

PRIOR ART

The relationship between cholesterol and *P. multiflorum* was investigated by Guo and Song in 1986. Guo, G. and Song, Z., *Effect of Shouwuyanshoudan and Nicotinic Acid on Serum Cholesterol in Pigeons Fed Hypercholesterolemic Diets*, J. Tianjing Medicine and Pharmacology 8: 40–42 (1986). In their study, eighty pigeons were fed a hypercholesterolemic diet and were divided into three groups: a *P. multiflorum* supplemented (2 g/day) group (n=20), a nicotinic acid supplemented (100 mg/day) group (n=20), and a control group (n=40). After two months, all pigeons, except 24 in the control group, were sacrificed. The 24 pigeons were divided into two groups again as a *P. multiflorum* supplemented group and a control group. The results of this study showed that mean serum cholesterol levels for both the *P. multiflorum* supplemented and nicotinic acid supplement groups were significantly decreased as compared to the control group. In the continued study of the 24 pigeons, serum cholesterol was also significantly decreased in the *P. multiflorum* supplemented group as compared to the control group. In sum, the study showed the hypocholesterolemic effect of *P. multiflorum* supplementation in pigeons fed a hypercholesterolemic diet.

Another study of the effects of *P. multiflorum* on cholesterol and related enzymes in rats was conducted by Niou, et al. in 1988. Niou, J., et al., *The Protective Effect Of Baishouwu on the Liver of Hyperlipidemic Rats*, ACTA Medicine Sinica, 3:26–27 (1988). In this study, groups fed a hypercholesterolemic diet including either powdered *P. multiflorum* or an extract from *P. multiflorum* showed significantly decreased serum cholesterol levels as compared to the group fed the hypercholesterolemic diet alone. Additionally, there were many neutral fat drops in the lobules of the liver in the group fed the hypercholesterolemic diet. Both *P. multiflorum* supplemented groups had very few fat drops and compared favorably to a normal diet group. The results suggested that *P. multiflorum* could be considered as a hypolipidemic agent.

More lipidemic indices and atherosclerotic changes tied to the use of *P. multiflorum* have been investigated in the Japanese quail by Wang and Jin. Wang, W. and Jin, D., *Ethanol Extract of Zhishouwu in Preventing Atherosclerosis of Japanese Quail*, Journal of Chinese Medicine Combined with Western Medicine 4: 748–750 (1984). In this trial, 46 Japanese quail were divided into four groups. These groups were fed hypercholesterolemic diets supplemented with water (control) or with small, medium or large doses of a *P. multiflorum* extract. The results showed that plasma HDL-cholesterol levels of the three *P. multiflorum* supplemented groups were increased as compared to the control group. Likewise, the HDL cholesterol/total cholesterol ratios in the three *P. multiflorum* supplemented groups were increased after 2–5 weeks. Moreover, plasma cholesterol and cholesterol esters in the three *P. multiflorum* supplemented groups were decreased compared to the control group after six weeks. Plasma triglyceride levels were also decreased as compared to the control group. Further, atherosclerotic changes in the aorta with the three levels of *P. multiflorum* supplementation were less than in the control group, especially in the large dose supplementation group.

In another study, stimulation of the conversion of cholesterol to cholic acid in vitro utilizing three concentrations of *P. multiflorum* was observed by Xu and Li in 1987. The investigation showed that the lowest concentration was the best for stimulating conversion of cholesterol to cholic acid. Xu, C. and Li, Y., *The Effect of Heshouwu on Hepatic Cell Induced by (3H)-cholesterol in Vitro*, ACTA Chinese Medicine and Pharmacology 3:39–40 (1987).

The use of *P. multiflorum* in various products also has been disclosed in several unrelated patents. U.S. Pat. No. 4,797,421 divulges the use of *P. multiflorum* in a proanthocyanidin antioxidant compound. (Col. 9, 1.23–50). Extracts of knotgrass are disclosed as an ingredient in a deodorant in U.S. Pat. No. 4,883,651. Herbal smoking materials incorporating extracts of *P. multiflorum* were revealed in U.S. Pat. No. 5,135,010. (Col. 1, 1.52–61). Further, *P. multiflorum* was disclosed as a potential ingredient in a plant component said to be effective in the control of protozoal disease in U.S. Pat. No. 5,135,746. (Col. 4, 1.25–38). Still further, *Polygonum bistoria L.* was declared to be effective in the treatment of HIV related disease in vitro in U.S. Pat. No. 5,178,865. (Table 1, #30). Lastly, an extraction procedure for *P. multiflorum* resulting in an extract that is an isolation of two stilbene glycoside gallates together with galloyl procyandins is disclosed in Nonaka, G., et al., *Stilbene Glycoside Gallates and Proanthocyanidins from Polygonum multiflorum*, Phytochemistry, 21:429–432 (1982).

It can thus be appreciated that, until now, the physiological and chemical properties of *P. multiflorum* as related to glucose metabolism have gone almost entirely undiscovered.

FRACTIONATION AND EXPERIMENTATION

After isolating *P. multiflorum* as the Chinese herb exhibiting the highest insulin potentiating activity, a study was conducted concerning the effects of fractions from *P. multiflorum* on plasma glucose and cholesterol in mice fed a hypercholesterolemic diet. The purpose of this study was to test the effects of different fractions of *P. multiflorum* separated on a Sephadex G-25 column on glucose and cholesterol in mice fed hypercholesterolemic diets.

A sample of *P. multiflorum* was ground to a fine powder. (It is preferred that the root of *P. multiflorum* be utilized.) The powder was stirred at a medium speed with an excess 20:1 (w/v) of 0.1N $NH_4OH$ for 2 hours and then centrifuged at 1,000×g for 20 minutes. (The supernatant may be refrigerated until chromatographed.) The supernatant (10 ml) was applied to a medium grade Sephadex G-25 column (50–150 u of particle size, 60×2.6 cm) and was eluted with distilled deionized water. Three fractions were collected. The first fraction was manifested in a dark brown band, the second in a light brown band, and the third in a pinkish brown band. The three fractions were evaporated at room temperature to ⅓ of their original volume for Experiment 1 and to ¹⁄₁₀ of their original volume for Experiment 2. Each combination of fractions was prepared by mixing the appropriate fractions and equal concentrations were maintained. The plasma glucose and cholesterol were analyzed using enzymatic methods. Insulin was analyzed by radioimmunoassay.

In Experiment No. 1, thirty-nine male weanling mice were randomly assigned to four groups: Fraction 1, 2, 3, or the control. In experiment No. 2, sixty-one male weanling mice were randomly assigned to six groups: fraction 1 and 2; fraction 1 and 3; fraction 2 and 3; fraction 1 and 2 and 3; crude extract; or control. All mice were fed a hypercholesterolemic diet with 1.0% cholesterol and 0.5% cholic acid. Each mouse was given 100 microliters of fraction(s) or water orally by micropipette daily. Experiments 1 and 2 were terminated after 10 and 9 weeks, respectively.

The results showed that mean plasma glucose was decreased significantly by fractions 1; 1 and 2; and 1 and 3. Mean plasma insulin was significantly decreased by fractions 1 and 2; 1 and 3; 2 and 3; and fraction 1 and 2 and 3. No fraction(s) had hypocholesterolemic effects.

The mean plasma glucose in the fraction 1 supplemented group (245 mg/dl) was significantly decreased compared with the control group (294 mg/dl) (P<0.04) (See Table 3).

TABLE 3

PLASMA GLUCOSE, INSULIN, AND CHOLESTEROL IN MICE SUPPLEMENTED WITH FRACTION 1, 2, OR 3 OF EXTRACT (EXPERIMENT 1)[1]

| Group | Glucose (mg/dl) | Insulin (uU/ml) | Cholesterol (mg/dl) |
| --- | --- | --- | --- |
| Fract 1 | 244.8 ± 16.2 | 8.5 ± 5.0 | 243.6 ± 15.2 |
| Fract 2 | 257.0 ± 18.0 | 14.9 ± 5.5 | 261.7 ± 16.0 |
| Fract 3 | 249.4 ± 16.2 | 30.4 ± 4.9 | 238.1 ± 15.2 |
| Control | 293.9 ± 17.0 | 16.5 ± 5.5 | 247.5 ± 16.0 |

| Source of variation | Analysis of Variance P Value | | |
| --- | --- | --- | --- |
| F1 vs Ct | 0.04[2] | 0.29 | 0.86 |
| F2 vs Ct | 0.15 | 0.83 | 0.53 |

TABLE 3-continued

PLASMA GLUCOSE, INSULIN, AND CHOLESTEROL IN MICE SUPPLEMENTED WITH FRACTION 1, 2, OR 3 OF EXTRACT (EXPERIMENT 1)[1]

| F3 vs Ct | 0.07 | 0.07 | 0.67 |
| --- | --- | --- | --- |

[1]Values are means ± SEM; n = 9–10.
[2]Significant difference from control group.

The mean plasma glucose in mice supplemented with combinations of fraction 1 and 2 (195 mg/dl) or fraction 1 and 3 (188 mg/dl) was significantly decreased (P<0.04 and P<0.02, respectively) compared to the control group (See table 4).

TABLE 4

MEAN PLASMA GLUCOSE, INSULIN, AND CHOLESTEROL IN MICE SUPPLEMENTED WITH COMBINATIONS OF FRACTIONS FROM EXTRACT (EXPERIMENT 2)[1,2]

| Group | Glucose (mg/dl) | Insulin (uU/ml) | Cholesterol (mg/dl) |
| --- | --- | --- | --- |
| F1 & 2 | 194.6 ± 10.8[a] | 13.9 ± 2.6[d] | 209.7 ± 13.2 |
| F1 & 3 | 188.3 ± 11.4[b] | 11.2 ± 2.7[d] | 225.1 ± 14.0 |
| F2 & 3 | 197.6 ± 10.8 | 15.1 ± 2.6[d] | 240.0 ± 13.2[c] |
| F1 & 2 & 3 | 211.8 ± 10.8 | 21.8 ± 2.6[d] | 197.4 ± 13.2 |
| Extract | 214.7 ± 10.3 | 24.9 ± 2.4 | 196.4 ± 12.6 |
| Control | 225.2 ± 10.3 | 31.4 ± 2.4 | 193.6 ± 12.6 |

[1]Values are means ± SEM; n = 10–11.
[2]The significant differences from control (a: P < 0.05; b: P < 0.02; c: P < 0.01; d: P < 0.001.

The mean plasma insulin concentrations in groups supplemented with combinations of fraction 1 and 2, fraction 1 and 3, fraction 2 and 3, and fraction 1 and 2 and 3 were all significantly lower than the control group (Table 4).

No fraction alone, nor the combinations of fractions, decreased plasma cholesterol. In fact, the mean plasma cholesterol concentration in mice fed fraction 2 and 3 (240 mg/dl) was significantly (P<0.01) higher than the control group (194 mg/dl) (Table 4).

A significant hypoglycemic effect was found when fraction 1 was supplemented alone. The combination of fraction 1 and 2 or fraction 1 and 3 also lowered plasma glucose significantly. This might be explained by insulin potentiation. This effect was demonstrated by fraction 1, fraction 1 and 2, fraction 1 and 3. Each fraction, and the combinations of fractions, investigated caused a hypoglycemic effect instead of the hypocholesterolemic effect observed in previous studies.

In another study, the effects of fraction 1 on plasma glucose and cholesterol in obese mice fed a hypercholesterolemic diet was tested. The purpose of the study was to investigate a possible hypoglycemic effect connected with fraction 1 of *P. multiflorum* in older, obese mice.

For this study, fraction 1 was collected in the same fashion as the prior study and was evaporated to ⅓ of its original volume at room temperature. Nineteen obese male mice were randomly assigned to two groups: Fraction 1 or control. The mice were fed a casein-based hypercholesterolemic diet containing 1% cholesterol and 0.5% cholic acid. Each mouse was given 100 microliters of fraction 1 or water orally by micropipette daily. After seven weeks, the mice were fasted 14 hours and were then given an oral glucose load (1 mg glucose/g body weight as a 50% solution) 60 minutes before sacrifice. The mice were anesthetized and exsanguinated by heart puncture. Again, plasma glucose and cholesterol were analyzed using enzymatic methods, and insulin was analyzed by radioimmunoassay.

In this study, mean plasma glucose and insulin ratios were not affected by fraction 1 (See Table 5).

TABLE 5

MEAN VALUE OF GLUCOSE, INSULIN, AND CHOLESTEROL IN OBESE MICE SUPPLEMENTED WITH FRACTION 1 OF EXTRACT[1]

| GROUP | GLUCOSE (MG/DL) | INSULIN (uU/ml) | CHOLESTEROL (mg/dl) |
|---|---|---|---|
| FRACTION | 393.6 ± 72.3 | 63.7 ± 22.3 | 168.7 ± 39.0 |
| CONTROL | 417.3 ± 36.1 | 79.3 ± 25.6 | 237.1 ± 46.9 |
| P VALUE | 0.4 | 0.2 | 0.003[2] |

[1]Values are means ± SEM; n = 9–10.
[2]Significant difference from control group.

However, the mean plasma cholesterol in the group supplemented with fraction 1 (169±39 mg/dl) was significantly lower (P<0.003) than the control group (237±47 mg/dl) (Table 5). Here, fraction 1 played the same role as had been previously observed with crude extracts of *P. multiflorum* in pigeons, rats and Japanese quail.

Fraction 1 did not have a hypoglycemic effect in the older obese mice as it did in the weanling lean mice. However, there were many differences, such as animal model traits, weight, age, diets, length of the experiment, and blood sampling times that might have contributed to this result.

The claims and the specification describe the invention presented, and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiment set forth herein for purposes of exemplification, but is to be limited only by the scope of the attached claim or claims, including the full range of equivalency to which each element thereof is entitled.

What is claimed is:

1. In a host with an unduly elevated blood glucose concentration, a method for treating hyperglycemia, which comprises:
   a. grinding a sample of *Polygonum multiflorum* to obtain a fine powder;
   b. stirring said powder with 0.1N NH$_4$OH to obtain an extract;
   c. centrifuging said extract to obtain a supernatant;
   d. applying the supernatant to a medium grade separator column of Sephadex G-25 to obtain a first fraction having a dark brown color; and
   e. ingesting a blood glucose lowering effective amount of said first fraction.

2. In a host with an unduly elevated blood glucose concentration, a method for treating hyperglycemia, which comprises the administration of an a blood glucose lowering effective amount of a composition derived from an extract of *Polygonum multiflorum*, said *Polygonum multiflorum* having been ground, then stirred with 0.1N NH$_4$OH to obtain said extract, said extract having been centrifuged to obtain a supernatant, said supernatant having been eluted in a medium grade separator column of Sephadex G-25 to obtain said composition, said composition being selected from the group consisting of:
   (a) a first fraction eluted from said separator column, said first fraction being manifest in a dark brown band;
   (b) a combination of said first fraction and a second fraction eluted from said separator column, said second fraction being manifest in a light brown band;
   (c) a combination of said first fraction and a third fraction eluted from said separator column, said third fraction being manifest in a pinkish brown band;
   (d) a combination of said second fraction and said third fraction; and
   (e) a combination of said first fraction, said second fraction and said third fraction.

3. The method according to claim 2 wherein said first fraction, said second fraction and said third fraction of said group are evaporated to one-third of their original volumes.

4. The method according to claim 2 wherein said first fraction, said second fraction and said third fraction of said group are evaporated to one-tenth of their original volumes.

5. A composition for treating hyperglycemia derived from an extract of *Polygonum multiflorum*, said *Polygonum multiflorum* having been ground, then stirred with 0.1N NH$_4$OH to obtain said extract, said extract having been centrifuged to obtain a supernatant, said supernatant having been eluted in a medium grade separator column of Sephadex G-25 to obtain said composition, said composition being selected from the group consisting of:
   (a) a first fraction eluted from said separator column, said first fraction being manifest in a dark brown band;
   (b) a combination of said first fraction and a second fraction eluted from said separator column, said second fraction being manifest in a light brown band;
   (c) a combination of said first fraction and a third fraction eluted from said separator column, said third fraction being manifest in a pinkish brown band;
   (d) a combination of said second fraction and said third fraction; and
   (e) a combination of said first fraction, said second fraction and said third fraction.

6. The composition according to claim 5 wherein said first fraction, said second fraction and said third fraction of said group are evaporated to one-third of their original volumes.

7. The composition according to claim 5 wherein said first fraction, said second fraction and said third fraction of said group are evaporated to one-tenth of their original volumes.

* * * * *